United States Patent
Li et al.

(10) Patent No.: US 10,716,847 B2
(45) Date of Patent: Jul. 21, 2020

(54) HAEMOPHILUS INFLUENZAE FUSION PROTEIN AND CONSTRUCTION METHOD AND USE THEREOF

(71) Applicant: CANSINO BIOLOGICS INC., Tianjin (CN)

(72) Inventors: Junqiang Li, Tianjin (CN); Danqing Miao, Tianjin (CN); Mingming Yang, Tianjin (CN); Zhongqi Shao, Tianjin (CN); Tao Zhu, Tianjin (CN); Xuefeng Yu, Tianjin (CN)

(73) Assignee: CANSINO BIOLOGICS INC., Tianjin (CN)

(*) Notice: Subject to any disclaimer, the term of this patent is extended or adjusted under 35 U.S.C. 154(b) by 69 days.

(21) Appl. No.: 15/940,871

(22) Filed: Mar. 29, 2018

(65) Prior Publication Data
US 2018/0214541 A1    Aug. 2, 2018

Related U.S. Application Data

(63) Continuation of application No. PCT/CN2016/098520, filed on Sep. 9, 2016.

(51) Int. Cl.
| | | |
|---|---|---|
| A61K 39/02 | (2006.01) | |
| A61K 39/385 | (2006.01) | |
| A61K 39/102 | (2006.01) | |
| C07K 19/00 | (2006.01) | |
| C12N 15/62 | (2006.01) | |
| A61K 47/64 | (2017.01) | |
| A61K 39/00 | (2006.01) | |

(52) U.S. Cl.
CPC .......... *A61K 39/385* (2013.01); *A61K 39/102* (2013.01); *A61K 47/646* (2017.08); *C07K 19/00* (2013.01); *C12N 15/62* (2013.01); *A61K 2039/6087* (2013.01); *A61K 2039/70* (2013.01); *Y02A 50/476* (2018.01); *Y02A 50/484* (2018.01)

(58) Field of Classification Search
None
See application file for complete search history.

(56) References Cited

U.S. PATENT DOCUMENTS

| | | | | |
|---|---|---|---|---|
| 5,939,297 A | * | 8/1999 | Loosmore | ................ C12N 9/52 435/220 |
| 6,391,313 B1 | * | 5/2002 | Loosmore | .......... A61K 39/1045 424/193.1 |

FOREIGN PATENT DOCUMENTS

| | | | |
|---|---|---|---|
| CN | 101374859 | * | 2/2009 |
| WO | 2002100891 A2 | * | 12/2002 |

OTHER PUBLICATIONS

Wu (J. Med. Res. Dec. 31, 2014. 43(12): 22-25).*
Forsgren et al (Clin Infect Dis. 2008;46(5):726-731).*
Mikayama et al. (Nov. 1993. Proc.Natl.Acad.Sci. USA, vol. 90 : 10056-10060).*
Rudinger et al. (Jun. 1976. Peptide Hormones. Biol.Council. pages 5-7).*
Chothia et al (The EMBO Journal, 1986, 5/4:823-26).*
Greenspan et al (Nature Biotechnology 7: 936-937, 1999).*
Trinh et al (Mol Immunol. Jan. 2004;40(10):717-22).*

* cited by examiner

*Primary Examiner* — Jennifer E Graser
(74) *Attorney, Agent, or Firm* — Flener IP & Business Law; Zareefa B. Flener (57) ABSTRACT

Provided are a fusion protein and a construction method thereof. The fusion method consists of: a *Haemophilus influenzae* protein D and a Hin47 (Htra) protein. The fusion protein can serve as a protein vehicle for a *Haemophilus influenzae* polysaccharide-protein conjugate vaccine, thereby increasing immunogenicity of a polysaccharide antigen.

8 Claims, 3 Drawing Sheets
Specification includes a Sequence Listing.

SEQUENCE LISTING

<160> NUMBER OF SEQ ID NOS: 3

<210> SEQ ID NO 1
<211> LENGTH: 438
<212> TYPE: PRT
<213> ORGANISM: Haemophilus influenzae

<400> SEQUENCE: 1

```
Met Thr Leu Pro Ser Phe Val Ser Glu Gln Asn Ser Leu Ala Pro Met
1               5                   10                  15

Leu Glu Lys Val Gln Pro Ala Val Val Thr Leu Ser Val Glu Gly Lys
            20                  25                  30

Ala Lys Val Asp Ser Arg Ser Pro Phe Leu Asp Asp Ile Pro Glu Glu
        35                  40                  45

Phe Lys Phe Phe Phe Gly Asp Arg Phe Ala Glu Gln Phe Gly Gly Arg
    50                  55                  60

Gly Glu Ser Lys Arg Asn Phe Arg Gly Leu Gly Ser Gly Val Ile Ile
65                  70                  75                  80

Asn Ala Ser Lys Gly Tyr Val Leu Thr Asn Asn Ala Val Ile Asp Glu
                85                  90                  95

Ala Asp Lys Ile Thr Val Gln Leu Gln Asp Gly Arg Glu Phe Lys Ala
            100                 105                 110

Lys Leu Val Gly Lys Asp Glu Leu Ser Asp Ile Ala Leu Val Gln Leu
        115                 120                 125

Glu Lys Pro Ser Asn Leu Thr Glu Ile Lys Phe Ala Asp Ser Asp Lys
    130                 135                 140

Leu Arg Val Gly Asp Phe Thr Val Ala Ile Gly Asn Pro Phe Gly Leu
145                 150                 155                 160

Gly Gln Thr Val Thr Ser Gly Ile Val Ser Ala Leu Gly Arg Ser Thr
                165                 170                 175

Gly Ser Asp Ser Gly Thr Tyr Glu Asn Tyr Ile Gln Thr Asp Ala Ala
            180                 185                 190

Val Asn Arg Gly Asn Ser Gly Gly Ala Leu Val Asn Leu Asn Gly Glu
        195                 200                 205

Leu Ile Gly Ile Asn Thr Ala Ile Ile Ser Pro Ser Gly Gly Asn Ala
    210                 215                 220

Gly Ile Ala Phe Ala Ile Pro Ser Asn Gln Ala Ser Asn Leu Val Gln
225                 230                 235                 240

Gln Ile Leu Glu Phe Gly Gln Val Arg Arg Gly Leu Leu Gly Ile Lys
                245                 250                 255

Gly Gly Glu Leu Asn Ala Asp Leu Ala Lys Ala Phe Asn Val Ser Ala
            260                 265                 270

Gln Gln Gly Ala Phe Val Ser Glu Val Leu Pro Lys Ser Ala Ala Glu
        275                 280                 285

Lys Ala Gly Leu Lys Ala Gly Asp Ile Ile Thr Ala Met Asn Gly Gln
    290                 295                 300

Lys Ile Ser Ser Phe Ala Glu Ile Arg Ala Lys Ile Ala Thr Thr Gly
305                 310                 315                 320

Ala Gly Lys Glu Ile Ser Leu Thr Tyr Leu Arg Asp Gly Lys Ser His
                325                 330                 335

Asp Val Lys Met Lys Leu Gln Ala Asp Asp Ser Ser Gln Leu Ser Ser
            340                 345                 350

Lys Thr Glu Leu Pro Ala Leu Asp Gly Ala Thr Leu Lys Asp Tyr Asp
        355                 360                 365
```

```
Ala Lys Gly Val Lys Gly Ile Glu Ile Thr Lys Ile Gln Pro Asn Ser
        370                 375                 380

Leu Ala Ala Gln Arg Gly Leu Lys Ser Gly Asp Ile Ile Gly Ile
385                 390                 395                 400

Asn Arg Gln Met Ile Glu Asn Ile Arg Glu Leu Asn Lys Val Leu Glu
                405                 410                 415

Thr Glu Pro Ser Ala Val Ala Leu Asn Ile Leu Arg Gly Asp Ser Asn
            420                 425                 430

Phe Tyr Leu Leu Val Gln
            435

<210> SEQ ID NO 2
<211> LENGTH: 5
<212> TYPE: PRT
<213> ORGANISM: Artificial Sequence
<220> FEATURE:
<223> OTHER INFORMATION: Short chain polypeptide

<400> SEQUENCE: 2

Gly Gly Gly Gly Ser
1               5

<210> SEQ ID NO 3
<211> LENGTH: 347
<212> TYPE: PRT
<213> ORGANISM: Haemophilus influenzae

<400> SEQUENCE: 3

Asp Pro Ser Ser His Ser Ser Asn Met Ala Asn Thr Gln Met Lys Ser
1               5                   10                  15

Asp Lys Ile Ile Ile Ala His Arg Gly Ala Ser Gly Tyr Leu Pro Glu
            20                  25                  30

His Thr Leu Glu Ser Lys Ala Leu Ala Phe Ala Gln Gln Ala Asp Tyr
        35                  40                  45

Leu Glu Gln Asp Leu Ala Met Thr Lys Asp Gly Arg Leu Val Val Ile
    50                  55                  60

His Asp His Phe Leu Asp Gly Leu Thr Asp Val Ala Lys Lys Phe Pro
65                  70                  75                  80

His Arg His Arg Lys Asp Gly Arg Tyr Tyr Val Ile Asp Phe Thr Leu
                85                  90                  95

Lys Glu Ile Gln Ser Leu Glu Met Thr Glu Asn Phe Glu Thr Lys Asp
            100                 105                 110

Gly Lys Gln Ala Gln Val Tyr Pro Asn Arg Phe Pro Leu Trp Lys Ser
        115                 120                 125

His Phe Arg Ile His Thr Phe Glu Asp Glu Ile Glu Phe Ile Gln Gly
    130                 135                 140

Leu Glu Lys Ser Thr Gly Lys Lys Val Gly Ile Tyr Pro Glu Ile Lys
145                 150                 155                 160

Ala Pro Trp Phe His His Gln Asn Gly Lys Asp Ile Ala Ala Glu Thr
                165                 170                 175

Leu Lys Val Leu Lys Lys Tyr Gly Tyr Asp Lys Lys Thr Asp Met Val
            180                 185                 190

Tyr Leu Gln Thr Phe Asp Phe Asn Glu Leu Lys Arg Ile Lys Thr Glu
        195                 200                 205

Leu Leu Pro Gln Met Gly Met Asp Leu Lys Leu Val Gln Leu Ile Ala
    210                 215                 220

Tyr Thr Asp Trp Lys Glu Thr Gln Glu Lys Asp Pro Lys Gly Tyr Trp
```

-continued

```
              225                 230                 235                 240
Val Asn Tyr Asn Tyr Asp Trp Met Phe Lys Pro Gly Ala Met Ala Glu
                245                 250                 255

Val Val Lys Tyr Ala Asp Gly Val Gly Pro Gly Trp Tyr Met Leu Val
                260                 265                 270

Asn Lys Glu Glu Ser Lys Pro Asp Asn Ile Val Tyr Thr Pro Leu Val
                275                 280                 285

Lys Glu Leu Ala Gln Tyr Asn Val Glu Val His Pro Tyr Thr Val Arg
                290                 295                 300

Lys Asp Ala Leu Pro Glu Phe Phe Thr Asp Val Asn Gln Met Tyr Asp
305                 310                 315                 320

Ala Leu Leu Asn Lys Ser Gly Ala Thr Gly Val Phe Thr Asp Phe Pro
                325                 330                 335

Asp Thr Gly Val Glu Phe Leu Lys Gly Ile Lys
                340                 345
```

HAEMOPHILUS INFLUENZAE FUSION PROTEIN AND CONSTRUCTION METHOD AND USE THEREOF

CROSS-REFERENCE TO RELATED APPLICATION

This application is a continuation application of International patent application No. PCT/CN2016/098520, filed on Sep. 9, 2016, which claims the benefit and priority of Chinese patent application No. CN201510638297.9, filed on Sep. 30, 2015, each of which is incorporated herein by reference in its entirety and for all purposes.

FIELD OF THE INVENTION

The present invention relates to the technical field of the development of vaccine products, in particular to a *Haemophilus influenzae* fusion protein and a construction method and use thereof.

BACKGROUND OF THE INVENTION

*Haemophilus influenzae* (Hi) is a class of non-motile, spore-free, rod-shaped Gram-negative bacilli that live in the respiratory tract of normal people and are opportunistic pathogens, mainly causing upper respiratory infections, otitis media and pneumonia, as well as sepsis, meningitis and other serious infections in children.

*Haemophilus influenzae* can be divided into capsular (typeable) and non-capsular (nontypeable). The capsular *Haemophilus influenzae* can be classified into 6 serotypes, a, b, c, d, e and f according to the components of the capsular polysaccharide. The non-capsular is also called nontypeable *Haemophilus influenzae* (NTHI).

*Haemophilus influenzae* invasive diseases occur all over the world. *Haemophilus influenzae* serotype B (Hib) is the most toxic and the main pathogenic bacterium which can cause bacterial meningitis in children under 5 years of age. The incidence of *Haemophilus influenzae* serotype b has been declined significantly with the worldwide promotion and use of the Hib conjugate vaccine, which is developed based on *Haemophilus influenzae* serotype b capsular polysaccharide. The capsular polysaccharide is the major antigenic substance of *Haemophilus influenzae* and may induce a protective immune response in the human body, however, the capsular polysaccharide is a thymus-independent antigen, which can only produce weak IgM antibodies but does not lead to immune memory, and cannot effectively protect infants and children within 2 years of age. Vaccine developers conjugate the capsular polysaccharide to a protein carrier to form a polysaccharide-protein conjugate vaccine, wherein the protein carrier changes the polysaccharide antigen from the thymus-independent antigen to the thymus-dependent antigen, thereby activating T helper lymphocytes and prompting B cells to produce specific IgG antibodies The Hib conjugate vaccine is now widely used in the world. However, the Hib conjugate vaccine is effective only against *Haemophilus influenzae* serotype b, and cannot prevent infections by other serotypes of *Haemophilus influenzae* and nontypeable *Haemophilus influenzae*, resulting in a substantial increase in the infection rates of other serotypes of *Haemophilus influenzae* and nontypeable *Haemophilus influenzae*. For example, the nontypeable *Haemophilus influenzae* may cause otitis media (OM), the Egyptian biota of *Haemophilus influenzae* may cause epidemic conjunctivitis and Brazilian purpuric fever. Vaccines for the prevention of *Haemophilus influenzae* other than serotype b or nontypeable *Haemophilus influenzae* have not yet been approved so far in the world.

The D protein (HiD) is a lipoprotein on the surface of *Haemophilus influenzae* and has a relative molecular weight of 42 KDa. The D protein is highly conserved in all *Haemophilus influenzae* strains (including *Haemophilus influenzae* with and without capsule), and is a specific antigen of human immunoglobulin D. Although the D protein is effective in preventing otitis media caused by NTHi, HiD has a relatively low molecular weight and a weak immunogenicity.

Hin47 (also known as HtrA) is a heat shock protein expressed by *Haemophilus influenzae* under ambient pressure, which has serine protease activity. Hin47 is an important immune antigen, which can stimulate the body to produce B cells and T cell responses as evidenced by experiments, and thus its immunogenicity has been fully confirmed.

SUMMARY OF THE INVENTION

The technical problem to be solved by the present invention is to provide a fusion protein Hin47-HiD as a protein carrier of conjugate vaccines.

Another technical problem to be solved by the present invention is to provide a method for the construction of the above-mentioned fusion protein.

Another technical problem to be solved by the present invention is to provide the use of the above-mentioned fusion protein Hin47-HiD, wherein the fusion protein is used as a protein carrier in the conjugate vaccine of Hia and Hib for the development of a universal *Haemophilus influenzae* conjugate vaccine.

In order to solve the above technical problems, the technical solution of the present invention is provided as follows:

a *Haemophilus influenzae* fusion protein which is obtainable by fusion of *Haemophilus influenzae* HiD protein and *Haemophilus influenzae* Hin47 protein, namely Hin47-HiD, wherein the amino acid sequence of Hin47 is the sequence shown in SEQ ID No: 1, and the amino acid sequence of HiD is the sequence shown in SEQ ID No: 3.

Preferably, the above-mentioned *Haemophilus influenzae* fusion protein is obtainable by fusion of *Haemophilus influenzae* HiD protein mutant and/or *Haemophilus influenzae* Hin47 protein mutant, the mutant each has 80% or more homology with the wild-type protein thereof, and the mutant can maintain immunogenicity of not less than 70% of that of the wild-type protein.

Preferably, the fusion gene expression system for the above-mentioned *Haemophilus influenzae* fusion protein includes, but is not limited to, a prokaryotic expression system, a eukaryotic expression system and a yeast expression system.

Preferably, for the above-mentioned *Haemophilus influenzae* fusion protein, the gene encoding *Haemophilus influenzae* HiD protein and the gene encoding *Haemophilus influenzae* Hin47 protein (monomer proteins constituting the fusion protein) include, but are not limited to, their wild types and mutants.

Preferably, in the above-mentioned *Haemophilus influenzae* fusion protein, the Hin47-HiD is obtainable by fusion of Hin47 and HiD in a 1:1 ratio through a linker, and the linker enables the monomers of the Hin47 protein and the HiD protein to maintain their own unique conformations.

Preferably, in the above-mentioned *Haemophilus influenzae* fusion protein, the linker includes, but not limited to, G4 S, DL or EL, wherein the linker enables the Hin47 protein and the HiD protein monomers to maintain their own unique conformations.

Preferably, in the above-mentioned *Haemophilus influenzae* fusion protein, the linker is G4S with the sequence shown in SEQ ID No: 2.

Preferably, in the above-mentioned *Haemophilus influenzae* fusion protein, the composition form of a gene for the fusion protein is (n)Hin47-linker-(n)HiD, (n)HiD-linker-(n)Hin47, -linker-HiD-(Hin47-linker-HiD)n-linker-Hin47-, -linker-Hin47-(HiD-linker-Hin47)n-linker-HiD-, wherein n is 1-3, representing the number of copies of the genes for the monomers.

Preferably, in the above-mentioned *Haemophilus influenzae* fusion protein, the composition form of the gene for the fusion protein is -linker-(Hin47-linker-HiD-linker)n-Hin47-, -linker-(HiD-linker-Hin47-linker)n-HiD-, wherein n is 1-3, representing the number of copies of the genes for the monomers.

Preferably, the above-mentioned *Haemophilus influenzae* fusion protein Hin47-HiD, as a protein carrier of a conjugate vaccine, can effectively improve the immunogenicity of a polysaccharide antigen.

Preferably, the above-mentioned *Haemophilus influenzae* fusion protein Hin47-HiD, can be used as a protein carrier in the development of the conjugate vaccines in which polysaccharide antigens are active ingredients, wherein the conjugate vaccines include, but not limited to, vaccines against *Haemophilus influenzae*, pneumonia, meningitis, dysentery, typhoid, and the like.

The present invention provides a broad-spectrum vaccine of *Haemophilus influenzae* polysaccharide-protein conjugate which is prepared by using one or more capsular polysaccharide(s) in *Haemophilus influenzae* serotype a, b, c, d, e and f as antigen(s), and Hin47-HiD as a protein carrier.

Preferably, in the above-mentioned broad-spectrum vaccine of *Haemophilus influenzae* polysaccharide-protein conjugate, the polysaccharide antigen component can effectively prevent the corresponding *Haemophilus influenzae* serotype(s), and the protein carrier component can prevent the nontypeable *Haemophilus influenzae*.

Preferably, the above-mentioned broad-spectrum vaccine of *Haemophilus influenzae* polysaccharide-protein conjugate, is a bivalent conjugate vaccine comprising a conjugate of Hia with the protein carrier Hin47-HiD and a conjugate of Hib with the protein carrier Hin47-HiD.

Preferably, in the above-mentioned broad-spectrum vaccine of *Haemophilus influenzae* polysaccharide-protein conjugate, the formulation of the bivalent conjugate vaccine is in a liquid form or a freeze-dried powder, each dose containing 8-15 μg of polysaccharide serotype a, 8-15 μg of polysaccharide serotype b and 20-80 μg of Hin47-HiD.

Preferably, in the above-mentioned broad-spectrum conjugate of *Haemophilus influenzae* polysaccharide-protein conjugate, the formulation of the bivalent conjugate vaccine is in a liquid form, each 0.5 ml dose containing 8-15 μg of polysaccharide serotype a, 8-15 μg of polysaccharide serotype b and 20-80 μg of Hin47-HiD.

Preferably, in the above-mentioned broad-spectrum vaccine of *Haemophilus influenzae* polysaccharide-protein conjugate, the bivalent conjugate vaccine contains no preservatives and may contain adjuvants, including but not limited to aluminum phosphate, and the buffer solution which is PB and NaCl, with a final concentration of 0.45% NaCl+10 mM PB.

The above-mentioned method for the construction of the fusion protein involves specific steps as follows:

(1) DNA synthesis:

a fusion gene comprising one copy of the Hin47 gene and one copy of the HiD gene, with Hin47 in the upstream of HiD, and the designed restriction site in the 5' of the fusion gene being NdeI and in the 3' being BamHI;

(2) Cloning of the fusion gene on the T-vectror:

subjecting the fusion gene to double-digestion with NdeI and BamHI, ligating with a T vector double-digested with the same endonucleases through T4 DNA ligase, transforming into a DH5a competent cell, extracting the plasmid and confirming by PCR and double-digestion;

(3) Construction of the expression vector:

subjecting the T clone to double-digestion with NdeI and BamHI to obtain the fusion gene, ligating with pET9a double-digested with the same endonucleases, transforming into a BL21 competent cell, then verifying the expression vector by double-digestion and PCR;

(4) Testing of the expression:

picking a positive monoclonal colony, culturing in LB medium, centrifuging, collecting the precipitate, redissolving the precipitate with PBS, breaking by sonication, and subjecting the supernatant to SDS-PAGE electrophoresis.

Preferably, the above-mentioned method for the construction of the fusion protein has the specific steps as follows:

(1) DNA synthesis:

synthesizing the Hin47-HiD fusion gene by Life Technologies Corporation, wherein the selected linker being G4S (GGGGS), the fusion gene comprising one copy of the gene for Hin47 and one copy of the gene for HiD, with Hin47 in the upstream of HiD, and the designed restriction site in the 5' of the fusion gene being NdeI and in the 3' being BamHI, wherein, the amino acid sequence of Hin47 being the sequence shown in SEQ ID No: 1, the amino acid sequence of the Linker being the sequence shown in SEQ ID No: 2, and the amino acid sequence of HiD being the sequence shown in SEQ ID No: 3, from which it can be seen that the Hin47-HiD fusion protein contains 790 aa and has a molecular weight of 87 KDa;

The amino acid sequence of the Hin47-HiD fusion protein

| | Amino acid sequence |
|---|---|
| Hin47 | MTLPSFVSEQNSLAPMLEKVQPAVVTLSVEGKAKVDSRSPFLD<br>DIPEEFKFFFGDRFAEQFGGRGESKRNFRGLGSGVIINASKGY<br>VLTNNAVIDEADKITVQLQDGREFKAKLVGKDELSDIALVQLE<br>KPSNLIEIKFADSDKLRVGDFTVAIGNPFGLGQTVTSGIVSAL<br>GRSTGSDSGTYENYIQTDAAVNRGNSGGALVNLNGELIGINTA<br>IISPSGGNAGIAFAIPSNQASNLVQQILEFGQVRRGLLGIKGG<br>ELNADLAKAFNVSAQQGAFVSEVLPKSAAEKAGLKAGDIITAM<br>NGQKISSFAEIRAKIATTGAGKEISLTYLRDGKSHDVKMKLQA<br>DDSSQLSSKIELPALDGATLKDYDAKGVKGIEITKIQPNSLAA<br>QRGLKSGDIIIGINRQMIENIRELNKVLETEPSAVALNILRGD<br>SNFYLLVQ |
| Linker | GGGGS |
| HiD | DPSSHSSNMANTQMKSDKIIIAHRGASGYLPEHTLESKALAFA<br>QQADYLEQDLAMTKDGRLVVIHDHFLDGLTDVAKKFPHRHRKD<br>GRYYVIDFTLKEIQSLEMIENFETKDGKQAQVYPNRFPLWKSH<br>FRIHTFEDEIEFIQGLEKSTGKKVGIYPEIKAPWFHHQNGKDI<br>AAETLKVLKKYGYDKKTDMVYLQIFDFNELKRIKTELLPQMGM<br>DLKLVQLIAYTDWKETQEKDPKGYWVNYNYDWMFKPGAMAEVV<br>KYADGVGPGWYMLVNKEESKPDNIVYTPLVKELAQYNVEVHPY<br>TVRKDALPEFFTDVNQMYDALLNKSGATGVFTDFPDTGVEFLK<br>GIK |

(2) Cloning of the fusion gene on the T vector:

subjecting the fusion gene to double-digestion with NdeI and BamHI, ligating with a T vector double-digested with the same endonuclease through T4 DNA ligase, transforming into a DH5a competent cell extracting the plasmid and identifying by PCR and double-digestion;

(3) Construction of the expression vector:

subjecting the T clone to double-digestion with NdeI and BamHI to obtain the fusion gene, ligating with pET9a double-digested with the same endonucleases, transforming into a BL21 competent cell, then confirming the expression vector by double-digestion and PCR;

(4) Testing of the expression:

picking a positive monoclonal colony, transferring to LB medium, culturing at 37° C. while shaking at 200 rpm overnight, transferring to 50 ml fresh LB medium, when $OD_{600}$=0.6-0.7, adding IPTG to a final concentration of 1 mM, inducing at 37° C. for 4 hours, centrifuging and collecting the precipitate, redissolving the precipitate with PBS, breaking by sonication, subjecting the supernatant to SDS-PAGE electrophoresis. The results show that the constructed expression strain, when induced by IPTG, successfully expresses the target protein.

It should be noted that the techniques used in the above-mentioned construction and induction of the expression of the fusion protein Hin47-HiD are routine experimental procedures known to those skilled in the art and are available in published literature and in books.

The above-mentioned purification method of the fusion protein Hin47-HiD has the specific steps as follows:

(1) Bacterial fermentation fermenting bacteria by conventional methods, which can be found in the published literature or known to those skilled in the art; inoculating the bacterial cells in LB medium, shaking at 250 rpm overnight at 37° C.; transferring the overnight culture to a 2 L flask containing 1 L medium, when $OD_{600}$=0.6-0.7, adding IPTG to a final concentration of 1 mM, inducing expression for 4 hours, centrifuging at 8000 rpm for 30 minutes and collecting the bacterial precipitate;

(2) Protein purification after the fermentation is completed, centrifuging and collecting the bacterial precipitate, redissolving the precipitate with PBS, breaking by sonication, centrifuging and collecting the supernatant, passing the supernatant through a Q column, collecting the flowthrough liquid (the target protein flows through); passing the Q column flowthrough liquid through a CHT column, using 150 mM PB+170 mM NaCl to wash the column, and 175 mM PB+1 M NaCl to elute the target protein.

The target protein with a purity of 80% or higher can be obtained by the two-step column purification and can be used in the subsequent development of the conjugate vaccine.

A preparation method of Hia and Hib bivalent conjugate vaccine has the specific steps as follows:

(1) Capsular polysaccharides purification and testing preparing the polysaccharide antigen by common methods, specifically including culturing *Haemophilus influenzae* by fermentation, subjecting the crude product to fractional precipitation with CTAB or ethanol, further recovering the capsular polysaccharide antigen by CL-4B gel separation, then dialyzing and freeze-drying;

the methods for the purification and identification of capsular polysaccharides of *Haemophilus influenzae* serotype a and serotype b can be found in the published literature;

(2) Preparation of the conjugate bulks of Hia and Hib preparation of the Hia conjugate vaccine: after adding serotype a capsular polysaccharide to CDAP (which is cyano-4-dimethylaminopyridine tetrafluoroborate) for 30 s, adding 0.2 M TEA to adjust the pH to 9.5 to activate the polysaccharide for 2.5 min; adjusting the pH to 9.0 and then adding the carrier protein according to the ratio of polysaccharide to protein of 1:1, reacting at room temperature for 1 h, keeping the resulting mixture at 4° C. overnight, then adding 2 M glycine to terminate the reaction; dialyzing to remove the reaction reagents, separating and purifying the conjugate by CL-4B gel; or preparation of the Hib conjugate vaccine: after adding serotype b capsular polysaccharide to CDAP for 30 s, adding 0.2 M TEA to adjust the pH to 9.5 to activate the polysaccharide for 2.5 min; adjusting the pH to 9.0 and then adding the carrier protein according to the ratio of polysaccharide to protein of 1:1, reacting at room temperature for 1 h, keeping the resulting mixture at 4° C. overnight, adding 2 M glycine to terminate the reaction; dialyzing to remove the reaction reagents, separating and purifying the conjugate by CL-4B gel;

(3) Preparation of Hia and Hib bivalent conjugate vaccine the recommended final lot preparation contains 10 ug (polysaccharide content) of Hia and Hib conjugate, 0.45% NaCl and 10 mM PB per dose; the product prepared based on above mentioned formulation can provide sufficient protection for the immunized population;

according to the final formulation and the concentration of the conjugate bulk, calculating the required amount of the conjugate bulk; taking the predetermined amount of conjugate bulk, adding PB and NaCl and then supplementing WFI so that the final concentration of Hia and Hib in the conjugate is 20 ug/ml (polysaccharide content), the final concentration of NaCl is 0.9%, and the final concentration of PB is 20 mM; distributing to obtain the final lot;

(4) Immunogenicity study of bivalent conjugate vaccine of Hia and Hib the animals can produce antibody reactions against Hia capsular polysaccharide and Hib capsular polysaccharide, and antibody reaction against the carrier protein can also be generated after being immunized with the above-mentioned Hia and Hib bivalent conjugate vaccine in a ¼ dose (125 μl); wherein the antibody against Hia capsular polysaccharide can effectively prevent *Haemophilus influenzae* serotype a, the antibody against Hib capsular polysaccharide can effectively prevent *Haemophilus influenzae* serotype b, and the antibody against the carrier protein (Hin47, HiD) can effectively prevent non-typeable *Haemophilus influenzae*.

The beneficial effects of the present invention are as follows:

the Hin47-HiD fusion protein can effectively enhance the immunogenicity of individual protein antigen of Hin47 and HiD; furthermore, the fusion protein Hin47-HiD can effectively enhance the immunogenicity of the polysaccharide antigens as a protein carrier of the conjugate vaccine; the fusion protein Hin47-HiD can be used as a protein carrier of the conjugate vaccine to develop a Hia conjugate vaccine, a Hib conjugate vaccine, and a bivalent vaccine containing the Hia conjugate vaccine and Hib conjugate vaccine.

DETAILED DESCRIPTION OF THE INVENTION

The technical solution of the present invention is further described below with reference to specific examples.

Example 1: Preparation of the Fusion Protein Hin47-HiD (1) Construction of the Hin47-HiD Expression Vector The Hin47-HiD fusion gene was synthesized by Life Technologies Corporation, wherein the selected linker was G4S (GGGGS), the fusion gene comprised one copy of the gene for Hin47 and one copy of the gene for HiD, with Hin47 in the upstream of HiD, and the designed restriction site in the 5' of the fusion gene being NdeI and in the 3' being BamHI, wherein the amino acid sequence of Hin47 was the sequence shown in SEQ ID No: 1, the amino acid sequence of the Linker was the sequence shown in SEQ ID No: 2, and the amino acid sequence of the HiD was the sequence shown in SEQ ID No: 3, see Table 1 below for details.

TABLE 1

Amino acid sequence of fusion protein Hin47-HiD

| | Amino acid sequence |
|---|---|
| Hin47 | MTLPSFVSEQNSLAPMLEKVQPAVVTLSVEGKAKVDSRSPFLD DIPEEFKFFFGDRFAEQFGGRGESKRNFRGLGSGVIINASKGY VLTNNAVIDEADKITVQLQDGREFKAKLVGKDELSDIALVQLE KPSNLTEIKFADSDKLRVGDFTVAIGNPFGLGQTVTSGIVSAL GRSTGSDSGTYENYIQTDAAVNRGNSGGALVNLNGELIGINTA IISPSGGNAGIAFAIPSNQASNLVQQILEFGQVRRGLLGIKGG ELNADLAKAFNVSAQQGAFVSEVLPKSAAEKAGLKAGDIITAM NGQKISSFAEIRAKIATTGAGKEISLTYLRDGKSHDVKMKLQA DDSSQLSSKTELPALDGATLKDYDAKGVKGIEITKIQPNSLAA QRGLKSGDIIIGINRQMIENIRELNKVLETEPSAVALNILRGD SNFYLLVQ |
| Linker | GGGGS |
| HiD | DPSSHSSNMANTQMKSDKIIIAHRGASGYLPEHTLESKALAFA QQADYLEQDLAMTKDGRLVVIHDHFLDGLTDVAKKFPHRHRKD GRYYVIDFTLKEIQSLEMTENFETKDGKQAQVYPNRFPLWKSH FRIHTFEDEIEFIQGLEKSTGKKVGIYPEIKAPWFHHQNGKDI AAETLKVLKKYGYDKKTDMVYLQTFDFNELKRIKTELLPQMGM |

TABLE 1-continued

Amino acid sequence of fusion protein Hin47-HiD

| | Amino acid sequence |
|---|---|
| | DLKLVQLIAYTDWKETQEKDPKGYWVNYNYDWMFKPGAMAEVV KYADGVGPGWYMLVNKEESKPDNIVYTPLVKELAQYNVEVHPY TVRKDALPEFFTDVNQMYDALLNKSGATGVFTDFPDTGVEFLK GIK |

As can be seen from Table 1, the Hin47-HiD fusion protein contains 790 aa and has a molecular weight of 87 kD.

The fusion gene was double-digested with NdeI and BamHI, ligated with a T vector double-digested with the same endonucleases using T4 DNA ligase, the resulting plasmid was transformed into DH5a competent cells, and extracted and verified by PCR and double-digestion.

The T clone was double-digested with NdeI and BamHI to obtain the fusion gene, which was ligated with pET9a double-digested with the same endonucleases, the fusion gene on the expression plasmid was transformed into BL21 competent cells, and the expression vector was confirmed by double-digestion and PCR.

Figure 1:
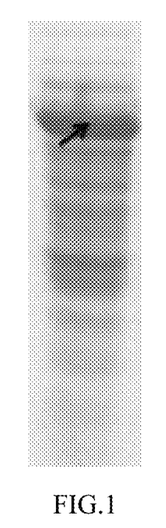
FIG. 1 illustrates the testing of the expression of the fusion protein.

The positive monoclonal colonies were picked, transferred to LB medium, cultured at 37° C. and shaken at 200 rpm overnight, transferred to 50 ml fresh LB medium, when $OD_{600}$=0.6-0.7, IPTG at a final concentration of 1 mM was added, and after induction at 37° C. for 4 hours, the cell pellet was collected by centrifugation. The precipitate was redissolved with PBS and sonicated, and the supernatant was subjected to SDS-PAGE electrophoresis to analyze whether the protein was expressed, the result is shown in FIG. 1:

FIG. 1 shows that the fusion protein was highly expressed in the supernatant.

It should be noted that the techniques used in the construction of the expression vector for the fusion protein Hin47-HiD and the induced expression are routine experimental procedures known to those skilled in the art and are available in published literature and in books.

(2) Purification of the fusion protein Hin47-HiD

The bacterial cells expressing Hin47-HiD were grown overnight, and then transferred to fermentation medium. When $OD_{600}$=0.6-0.7, IPTG was added to a final concentration of 1 mM, and after induction at 37° C. for 4 hours, the bacteria was subjected to centrifugation to collect precipitate.

The precipitate was redissolved with PBS, sonicated, and centrifuged to collect the supernatant. The supernatant was passed through a Q column to collect the flowthrough liquid (the target protein flowed through), then the Q column flowthrough liquid was passed through a CHT column, and 150 mM PB+170 mM NaCl was used to wash the column, and 175 mM PB+1 M NaCl was used to elute the target protein. The purification process is advantageous since it has simple steps, can make use of conventional fillers, and can produce the target protein with the purity of 80% or higher with only two steps. The result is shown in FIG. 2.

Figure 2:
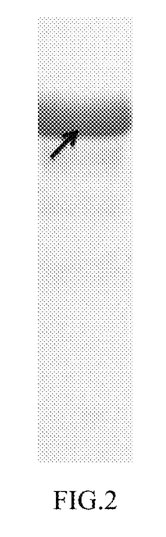
FIG. 2 illustrates the purification process of the fusion protein Hin47-HiD.

As can be seen from FIG. 2, the target protein with a purity of 80% or higher can be obtained by the two-step column purification.

Example 2: Study on Immunogenicity of the Fusion Protein Hin47-HiD

BALB/C mouse was immunized with the fusion protein Hin47-HiD three times at intervals of two weeks to study its immunogenicity, with Hin47 and HiD as controls. Whole blood was collected 14 days after the last immunization, and serum antibody levels were tested.

In the control groups, the immunization doses of the Hin47 or HiD protein antigen were 1 μg, 5 μg and 10 μg, respectively, while in the immunization group of the fusion protein, the doses of the protein monomer were 1 μg, 5 μg and 10 μg, respectively.

Figure 3:
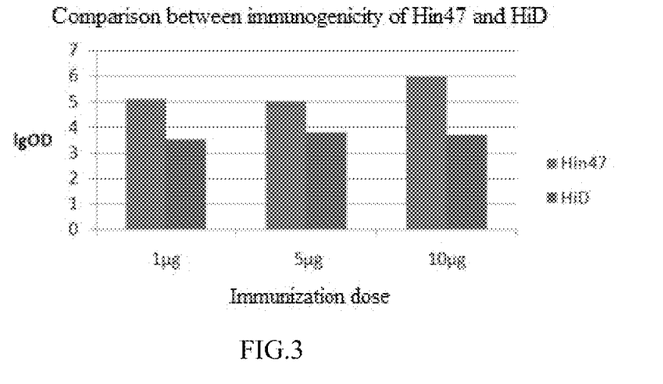
FIG. 3 illustrates the comparison between immunogenicity of Hin47 and HiD

The mice were immunized with Hin47 and HiD antigens in three doses of 1 μg, 5 μg and 10 μg, respectively, and the antibody titers of the three immune sera were tested with the corresponding antigens, the results are shown in FIG. 3.

Statistical Analysis:
P(Hin47 1 μg: HiD 1 μg)=0.000<0.01
P(Hin47 5 μg: HiD 5 μg)=0.000<0.01
P(Hin47 10 μg: HiD 10 μg)=0.000<0.01

The results showed that Hin47 generates a stronger immune response than HiD at the same dose.

The immunogenicity of the fusion protein Hin47-HiD was studied in three doses, and the actual immunization dose of the protein monomer in the fusion protein was the same as that of the control antigen (Hin47 or HiD). In the comparison experiment for the immunogenicity between Hin47-HiD and Hin47, the three groups L, M and H represented the doses of Hin47 monomer antigen in the fusion protein of 1 μg, 5 μg and 10 μg, respectively.

Figure 4:
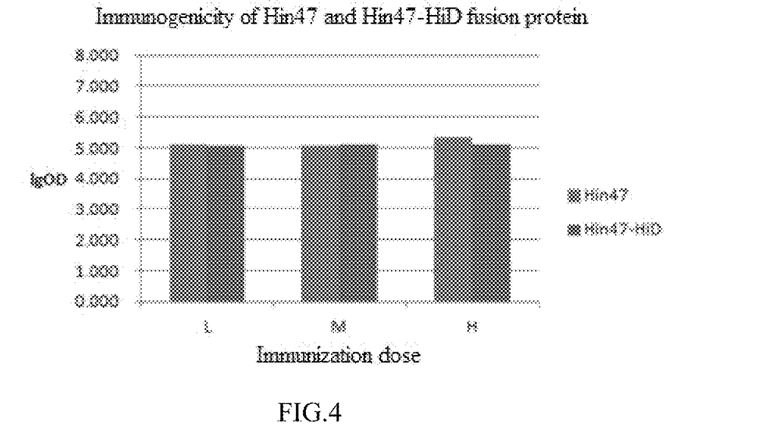
FIG. 4 illustrates the comparison of anti-Hin47 immunogenicity between Hin47 and Hin47-HiD, wherein, the immunization dose of the Hin47 monomer in the fusion protein Hin47-HiD is the same as that of the Hin47 antigen in the control group, wherein L, M and H indicate that the dose of the Hin47 monomer antigen (including Hin47 in control group) in fusion protein Hin47-HiD is 1 μg, 5 μg and 10 μg, respectively.

The comparison of the immunogenicity between Hin47 and Hin47-HiD is shown in FIG. 4.

Statistical Analysis:
P(L group Hin47: Hin47-HiD)=0.2820> 0.05
P(M group Hin47: Hin47-HiD)=0.2820> 0.05
P(H group Hin47: Hin47-HiD)=0.350> 0.05

The results show that the fusion protein Hin47-HiD does not affect the immunogenicity of Hin47.

The immunogenicity of the fusion protein Hin47-HiD was studied in three doses, and the actual immunization dose of the protein monomer in the fusion protein was the same as that of the control antigen (Hin47 or HiD). In the comparison experiment for the immunogenicity between Hin47-HiD and HiD, the three groups L, M and H represented the doses of HiD monomer antigen in the fusion protein of 1 μg, 5 μg and 10 μg, respectively.

Figure 5:
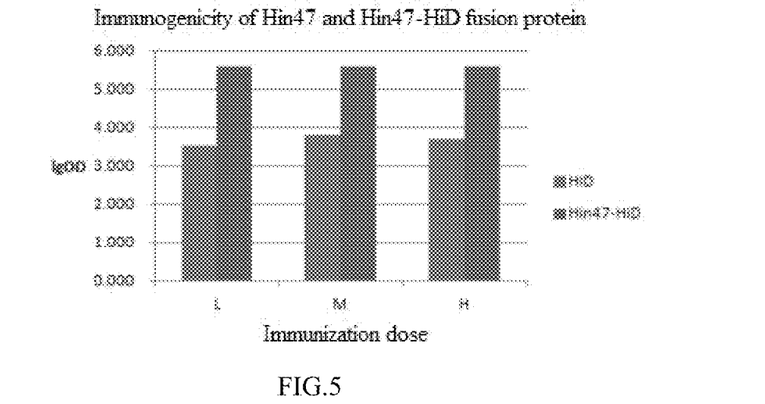
FIG. 5 illustrates the comparison of anti-HiD immunogenicity between HiD and Hin47-HiD, wherein the immunization dose of the HiD monomer in the fusion protein Hin47-HiD is the same as that of the HiD antigen in the control group, wherein L, M and H indicate that the dose of the HiD monomer antigen (including HiD in the control group) in the fusion protein Hin47-HiD is 1 μg, 5 μg and 10 μg, respectively.

The comparison of the immunogenicity between HiD and Hin47-HiD is shown in FIG. 5.

Statistical Analysis:
P(L group HiD: Hin47-HiD)=0.000<0.01
P(M group HiD: Hin47-HiD)=0.000<0.01
P(H group HiD: Hin47-HiD)=0.000<0.01

The results show that the Hin47-HiD fusion protein can effectively enhance the immunogenicity of HiD.

Example 3: Preparation of Hia and Hib Conjugate Bulks

Polysaccharide-protein conjugates of polysaccharide Hia and Hib were prepared by using the same method. Specifically, after adding the capsular polysaccharide to CDAP for 30 seconds, 0.2 M TEA was added to adjust the pH to 9.5 for polysaccharide activation, and the activation was continued for 2.5 min, after the activation, the pH was adjusted to 9.0, Hin47-HiD fusion protein was added according to a ratio of polysaccharide to protein of 1:1, the reaction was carried out at room temperature for 1 hour, the resulting mixture was kept at 4° C. overnight, and then 2 M glycine was added to terminate the reaction; the resulting mixture was dialyzed to remove the reaction reagents, and the conjugate was separated and purified by CL-4B gel.

Figure 6:
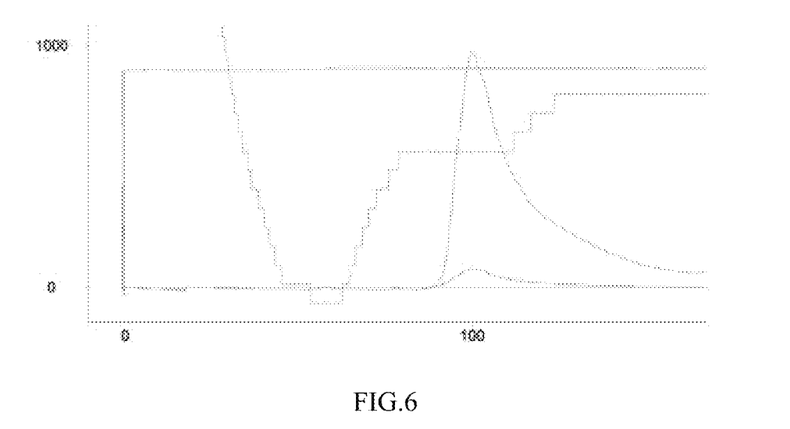
FIG. 6 illustrates the purification process of Hia conjugate.

The CL-4B gel separation result of Hia conjugate is shown in FIG. 6.

Figure 7:
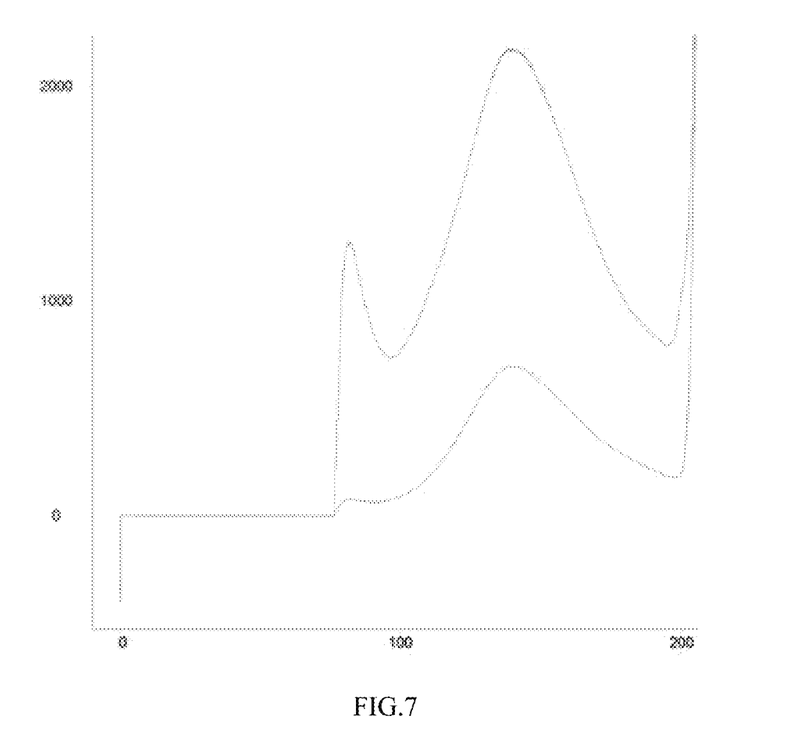
FIG. 7 illustrates the purification process of Hib conjugate.

The CL-4B gel separation result of Hib conjugate is shown in FIG. 7.

TABLE 2

Testing results of Hia and Hib bivalent conjugate vaccine

| Name of conjugate | Polysaccharide content mg/ml | Protein content mg/ml | Polysaccharide/ protein | Free polysaccharide | Free protein |
|---|---|---|---|---|---|
| Hia conjugate bulk | 3.5 | 7.21 | 0.485 | 13% | 4% |
| Hib conjugate bulk | 2.8 | 8.47 | 0.33 | 10% | 2% |

Example 4: Production of the Finished Product of Hia and Hib Bivalent Conjugate Vaccine, ie, Conjugate Vaccine Against *Haemophilus influenzae* Serotype a and Serotype b Taking the production of 200 vials of the vaccine as an example, in theory, 100 ml of the final bulk was required to prepare 200 vials of the final lot. According to the concentration of the conjugate bulk, 0.57 ml of Hia conjugate bulk, 0.72 ml of Hib conjugate bulk, 1 ml of 1 M PB, and 50 ml of NS were required, supplied with 47.7 ml of WFI, to obtain the final bulk, each vial was then filled with 0.5 ml to obtain the finished product.

The final lot contains 10 ug (polysaccharide content) of Hia conjugate and 10 μg Hib conjugate, 0.45% NaCl, and 10 mM PB per dose.

Example 5: Study on the Immunogenicity of the Conjugate Vaccine Against *Haemophilus influenzae* Serotype a and Serotype b The immunogenicity of the conjugate vaccine against *Haemophilus influenzae* serotype a and serotype b (with Hin47-HiD as the carrier protein) was evaluated according to the protocol for the efficacy test of the conjugate vaccine against *Haemophilus influenzae* serotype b as described in the Chinese Pharmacopoeia. Specifically, 10 BALB/C mice with weight of 12-14 g were immunized with the conjugate vaccine against *Haemophilus influenzae* serotype a and serotype b in ¼ human dose (containing Hia polysaccharide 2.5 μg and Hib polysaccharide 2.5 μg respectively), and 10 BALB/C mice were immunized with NS as the negative control, the immunization was performed 2 times at 2-week intervals, and eyeballs were removed to collect serum 14 days after the last immunization.

The titers of antibodies in serum against both capsular polysaccharide serotype-a and serotype-b were measured by ELISA, and the measurement of the serum samples of NS-immunized mice was used as the CUT off value to calculate the rate of positive immune response in the vaccine group. The results are shown in Table 3.

TABLE 3

Test results of immune responses with the conjugate vaccine against *Haemophilus influenzae* serotype a and serotype b

| Name of conjugate vaccine | Coating antigen | Dilution | Immune response rate |
|---|---|---|---|
| conjugate vaccine against *Haemophilus influenzae* serotype a and serotype b | capsular polysaccharide serotype a | 100 | 100% |
| | capsular polysaccharide serotype b | 100 | 100% |

The results show that: the fusion protein Hin47-HiD, as a protein carrier, can effectively stimulate the body to produce immune response to the polysaccharide antigens. In this example, the mice were immunized with the conjugate vaccine against *Haemophilus influenzae* serotype a and serotype b in ¼ human dose, and the response rate after two immunizations was 100%, which reached the release standard of Chinese Pharmacopoeia for the immunization efficacy of the Hib conjugate vaccine product.

Example 6: Study on the Protection of the Conjugate Vaccine Against *Haemophilus influenzae* Serotype a and Serotype b The content of specific antibodies in serum can be effectively measured by ELISA, however, not all antibodies have bactericidal protection function, and serum bactericidal antibodies (SBA) can reflect the functional activity of antibodies, which directly reflects the protective effects of the vaccine.

The test results of SBA in sera of mice immunized with the conjugate vaccine against *Haemophilus influenzae* serotype a and serotype b are shown in Table 4.

TABLE 4

Test results of SBA of the conjugate vaccine against *Haemophilus influenzae* serotype a and serotype b

| Name of conjugate vaccine | Bacterial strain | SBA |
|---|---|---|
| conjugate vaccine against *Haemophilus influenzae* serotype a and serotype b | *Haemophilus influenzae* serotype a | 1341 |
| | *Haemophilus influenzae* serotype b | 1560 |

In this example, the SBA in sera of mice immunized with the conjugate vaccine against *Haemophilus influenzae* serotype a and serotype b was as high as 1300, which can effectively prevent infection from *Haemophilus influenzae* serotype a and *Haemophilus influenzae* serotype b.

TABLE 5

Antibody titers against the carrier protein in the conjugate vaccine against *Haemophilus influenzae* serotype a and serotype b

| Name of conjugate vaccine | Titer of anti-Hin47 antigen antibody (GMT/lgOD) | Titer of anti-HiD antigen antibody (GMT/lgOD) |
|---|---|---|
| conjugate vaccine against *Haemophilus influenzae* serotype a and serotype b | 6.34 | 5.65 |

As can be seen from Table 5, the mice simultaneously produced antibodies to the carrier protein after being immunized with the conjugate vaccine against *Haemophilus influenzae* serotype a and serotype b, wherein the titer of anti-HiD antigen antibody was 5.65 and that of anti-Hin47 antigen antibody was up to 6.34. These antibodies could effectively prevent infection of non-typeable *Haemophilus influenzae*.

Protective results show that: after the mice are immunized with the conjugate vaccine against *Haemophilus influenzae* serotype a and serotype b, anti-Hia and anti-Hib polysaccharide antibodies can effectively prevent *Haemophilus influenzae* serotype a and *Haemophilus influenzae* serotype b, while antibodies against the carrier protein Hin47-HiD can effectively prevent non-typeable *Haemophilus influenzae*.

The application principle of the present invention may be as follows: the polysaccharide-protein conjugate vaccine can promote the thymus-independent polysaccharide antigen to become thymus-dependent, thereby making the polysaccharide antigen suitable for immunoprophylaxis in populations such as infants and children. The first generation of the conjugate vaccine protein carrier is tetanus toxoid TT and diphtheria toxoid DT, the second generation of the conjugate vaccine protein carrier is a non-toxic protein such as diphtheria toxin mutants CRM; the present invention belongs to a new generation of conjugate vaccine protein carrier, which is characterized in that in addition to effectively improving the immunogenicity of the polysaccharide antigens, antibodies against the carrier protein itself can also resist certain diseases. Hin47 and HiD have been shown to prevent non-typeable *Haemophilus influenzae*, whereas the Hin47-HiD fusion protein developed by the present invention can significantly improve the immunogenicity of the weak antigen HiD without affecting the immunogenicity of Hin47, and more importantly, the Hin47-HiD fusion protein can be effective as a conjugate vaccine protein carrier. Therefore, in the present invention, a novel conjugate vaccine protein carrier is developed, the conjugate vaccine developed by using it as a carrier can prevent the bacterial infection corresponding to polysaccharide antigen, in addition, antibodies against the carrier protein itself can prevent non-typeable *Haemophilus influenzae*.

The above detailed description of the *Haemophilus influenzae* fusion protein, the construction method and use thereof with reference to the above examples are intended to be illustrative and not limitative, and certain embodiments may be extended within the scope of the present invention. Therefore, any changes and modifications without departing from the general concept of the present invention should fall within the protection scope of the present invention.

The invention claimed is:

1. A *Haemophilus influenzae* fusion protein obtainable by fusion of *Haemophilus influenzae* HiD protein and *Haemophilus influenzae* Hin47 protein, wherein the amino acid sequence of Hin47 is the sequence shown in SEQ ID No: 1, and the amino acid sequence of HiD is the sequence shown in SEQ ID No: 3.

2. The fusion protein of claim 1, wherein the fusion protein is obtainable by fusion of Hin47 and HiD in a 1:1 ratio through a linker, the linker enables the monomers of Hin47 protein and HiD protein to maintain their own unique conformations.

3. The fusion protein of claim 2, wherein the linker is G4S with the sequence shown in SEQ ID No: 2.

4. The fusion protein of claim 1, wherein the composition form of a gene for the fusion protein is (n)Hin47-linker-(n)HiD, (n)HiD-linker-(n)Hin47, -linker-HiD-(Hin47-linker-HiD)n-linker-Hin47-, -linker-Hin47-(HiD-linker-Hin47)n-linker-HiD-, wherein n is 1-3, representing the number of copies of the genes for the monomers.

5. The fusion protein of claim 1, wherein the composition form of the gene for the fusion protein is -linker-(Hin47-linker-HiD-linker)n-Hin47-, -linker-(HiD-linker-Hin47-linker)n-HiD-, wherein n is 1-3, representing the number of copies of the genes for the monomers.

6. The fusion protein of claim 1, wherein the fusion protein is used as a protein carrier in the preparation of a conjugate vaccine using a polysaccharide antigen as an active ingredient.

7. The fusion protein of claim 6, wherein the conjugate vaccine is against *Haemophilus influenzae*, pneumonia, meningitis, dysentery or typhoid.

8. The fusion protein of claim 1, wherein the fusion protein is used as a protein carrier for a Hia and Hib conjugate vaccine, wherein Hia stands for a capsular polysaccharide in *Haemophilus influenzae* serotype a, and Hib stands for a capsular polysaccharide in *Haemophilus influenzae* serotype b.

* * * * *